(12) United States Patent
Coates et al.

(10) Patent No.: US 10,736,888 B2
(45) Date of Patent: Aug. 11, 2020

(54) TRIPLE COMBINATION

(71) Applicant: HELPERBY THERAPEUTICS LIMITED, Greater London (GB)

(72) Inventors: Anthony Coates, London (GB); Yanmin Hu, London (GB)

(73) Assignee: HELPERBY THERAPEUTICS LIMITED (GB)

( * ) Notice: Subject to any disclaimer, the term of this patent is extended or adjusted under 35 U.S.C. 154(b) by 0 days.

(21) Appl. No.: 15/770,674

(22) PCT Filed: Oct. 20, 2016

(86) PCT No.: PCT/GB2016/053277
§ 371 (c)(1),
(2) Date: Apr. 24, 2018

(87) PCT Pub. No.: WO2017/072488
PCT Pub. Date: May 4, 2017

(65) Prior Publication Data
US 2018/0311232 A1    Nov. 1, 2018

(30) Foreign Application Priority Data
Oct. 27, 2015 (GB) .................................. 1518969.9

(51) Int. Cl.
| | | |
|---|---|---|
| *A61K 9/00* | (2006.01) | |
| *A61K 31/4745* | (2006.01) | |
| *A61P 31/06* | (2006.01) | |
| *A61P 31/08* | (2006.01) | |
| *A61K 31/351* | (2006.01) | |
| *A61K 31/7036* | (2006.01) | |

(52) U.S. Cl.
CPC ........ *A61K 31/4745* (2013.01); *A61K 9/0014* (2013.01); *A61K 9/0053* (2013.01); *A61K 9/0073* (2013.01); *A61K 31/351* (2013.01); *A61K 31/7036* (2013.01); *A61P 31/06* (2018.01); *A61P 31/08* (2018.01); *A61K 2300/00* (2013.01); *Y02A 50/401* (2018.01); *Y02A 50/404* (2018.01); *Y02A 50/406* (2018.01); *Y02A 50/469* (2018.01); *Y02A 50/475* (2018.01); *Y02A 50/479* (2018.01); *Y02A 50/481* (2018.01); *Y02A 50/483* (2018.01)

(58) Field of Classification Search
CPC .............. A61K 31/351; A61K 31/4745; A61K 31/7036; A61K 9/0014; A61K 9/0073; A61K 2300/00
USPC ......................................................... 514/39
See application file for complete search history.

(56) References Cited

U.S. PATENT DOCUMENTS

| | | | |
|---|---|---|---|
| 6,974,585 B2 | 12/2005 | Askill | |
| 8,207,187 B2 * | 6/2012 | Beck | A61K 31/4439 514/292 |
| 8,940,723 B2 * | 1/2015 | Hu | A61K 31/155 514/187 |
| 9,216,186 B2 * | 12/2015 | Hu | A61K 31/4745 |
| 9,694,006 B2 * | 7/2017 | Beck | A61K 31/4439 |
| 9,789,101 B2 * | 10/2017 | Hu | A61K 31/351 |

FOREIGN PATENT DOCUMENTS

| | | |
|---|---|---|
| WO | 95/10999 A1 | 4/1995 |
| WO | 00/28074 A1 | 5/2000 |
| WO | 2005/014585 A1 | 2/2005 |
| WO | 2006/048747 A1 | 5/2006 |
| WO | 2007/054693 A1 | 5/2007 |
| WO | 2008/056151 A1 | 5/2008 |
| WO | 2008/117079 A1 | 10/2008 |
| WO | 2008/142384 A1 | 11/2008 |
| WO | 2012017215 | 2/2012 |
| WO | 2012017216 | 2/2012 |
| WO | WO 2012/017215 A1 * | 2/2012 ......... A61K 31/4745 |
| WO | WO 2012/017216 A1 * | 2/2012 ......... A61K 31/4745 |

OTHER PUBLICATIONS

Hu et al, J. Antimicrobial Chemotherapy, 2012, 68(2), pp. 1-11.*
L. Alou et al., In vitro activity of mupirocin and amoxicillin-clavulanate alone and in combination against staphylococci including those resistant to methicillin, J. Antimicrob. Agents, 23(5), 2004, pp. 513 to 516.
G.M.L. Bode et al., Preventing Surgical-Site Infections in Nasal Carriers of *Staphylococcus aureus*, N. Engl. J. Med., vol. 362, No. 1, Jan. 2010, pp. 9 to 17.
A. Coates et al., The future challenges facing the development of new antimicrobial drugs, Nature Reviews, Drug Discovery, vol. 1, Nov. 2002, pp. 895 to 910.
P. Davey et al., Tolerance of Pseudomonas aeruginosa to killing by ciprofloxatin, gentamicin and imipenem in vitro and in. vivo, J. Antimicrob. Chemother., 21, 1988, pp. 395 to 404.
C.A. Fux et al., Survival strategies of infectious biofilms, Trends in Microbiology, vol. 13, No. 1, Jan. 2005, pp. 34 to 40.
R. Ghiselli et al., Prophylaxis against *Staphylococcus aureus* Vascular Graft Infection with Mupirocin-Soaked, Collagen-Sealed Dacron. J. Surg. Res., vol. 99, No. 2, Aug. 2001, pp. 316 to 320.
R.D. Gonzales et al., Infections due to vancomycin-resistant Enterococcus faecium resistant to linezolid, Lancet, vol. 357, Apr. 14, 2001, pp. 1179.
K. Groicher et al., The *Staphylococcus aureus* lrgAB Operon Modulates Murein Hydrolase Activity and Penicillin Tolerance, J. Bacteriol., vol. 182, No. 7, Apr. 2000, pp. 1794 to 1801.

(Continued)

*Primary Examiner* — Ganapathy Krishnan
(74) *Attorney, Agent, or Firm* — McDonald Hopkins LLC (57) ABSTRACT

The invention provides a combination comprising 4-methyl-8-phenoxy-1-(2-phenylethyl)-2,3-dihydro-1H-pyrrolo[3,2-c]quinoline or a pharmaceutically acceptable derivative thereof, mupirocin or a pharmaceutically acceptable derivative thereof and neomycin or a pharmaceutically acceptable derivative thereof. This triple combination is particularly useful for the treatment and/or prevention of microbial infections.

16 Claims, 2 Drawing Sheets

(56) References Cited

OTHER PUBLICATIONS

Y. Hu and A. Coates, Increased levels of sigJ mRNA in late stationary phase cultures of Mycobacterium tuberculosis detected by DNA array hybridisation, FEMS Microbiol. Lett., 202, 2001, pp. 59 to 65.

Y. Hu et al., Detection of mRNA Transcripts and Active Transcription in Persistent Mycobacterium tuberculosis Induced by Exposure to Rifampin or Pyrazinamide, J. Bacteriol., vol. 182, No. 22, Nov. 2002, pp. 6358 to 6365.

D. Hughes and D.I. Andersson, Carbon starvation of *Salmonella typhimurium* does not cause a general increase of mutation rates, J. BacterioL, vol. 179, No. 21, Nov. 1997, pp. 6688 to 6691.

J.L. Martinez and F. Baguero, Mutation frequencies and antibiotic resistance, Antimicrob. Agents Chemother., vol. 44, No. 7, Jul. 2000, pp. 1771 to 1777.

G. Orhan et al., Synergy tests by E test and checkerboard methods of antimicrobial combinations against *Brucella melitensis*, J. Clin. Microbiol., vol. 43, No. 1, Jan. 2005, pp. 140 to 143.

T.M. Perl et al., Intranasal mupirocin to prevent postoperative *Staphylococcus aureus* infections, N. Engl. J. Med., vol. 346, No. 24, Jun. 2002, pp. 1871 to 1877.

A.L. Spoering and K. Lewis, Biofilms and Planktonic Cells of Pseudomonas aeruginosa Have Similar Resistance to Killing by Antimicrobials, J. Bacteriol., vol. 183, No. 23, Dec. 2001, pp. 6746 to 6751.

B.G. Spratt, Resistance to antibiotics mediated by target alterations, Science, vol. 264, Apr. 1994, pp. 388 to 393.

F. Taddei et al., cAMP-dependent SOS induction and mutagenesis in resting bacterial populations, Proc. Natl. Acad. Sci. USA, vol. 92, Dec. 1995, pp. 11736 to 11740.

S. Tsiodras et al., Linezolid resistance in a clinical isolate of *Staphylococcus aureus*, Lancet, vol. 358, Jul. 2001, pp. 207 to 208.

G.J. Van Asselt and R.P. Mouton, Detection of penicillin tolerance of *Streptococcus pyogenes*, J. Med. Microbiol., vol. 38, 1993, pp. 197 to 202.

Patent Cooperation Treaty (PCT), International Search Report and Written Opinion for Application PCT/GB2016/053277 filed Oct. 20, 2016, dated Dec. 21, 2016, International Searching Authority, EP.

Hu, et al., "Enhancement by novel anti-methicillin-resistant *Staphylococcus aureus* compound HT61 of the activity of neomycin, gentamicin, mupirocin and chlorhexidine: in vitro and in vivo studies." Journal of Antimicrobial Chemotherapy. vol. 68, No. 2, pp. 1-11, Oct. 4, 2012.

Patent Cooperation Treaty (PCT), International Preliminary Report on Patentability for Application PCT/GB2016/053277 filed Oct. 20, 2016, dated May 11, 2018, International Searching Authority, IB.

* cited by examiner

TRIPLE COMBINATION

CROSS-REFERENCE TO RELATED APPLICATION

This application is a 35 U.S.C. § 371 national stage filing of PCT Application No. PCT/GB2016/053277 filed on Oct. 20, 2016, which claims priority to Great Britain Patent Application No. 1518969.9 filed on Oct. 27, 2015, each of which are incorporated herein in their entirety by reference.

This invention relates to a combination of antimicrobial agents for the prevention and/or treatment of microbial infections. In particular, it relates to the use of 4-methyl-8-phenoxy-1-(2-phenylethyl)-2,3-dihydro-1H-pyrrolo[3,2-c]quinoline or a pharmaceutically acceptable derivative thereof in combination with mupirocin and neomycin or pharmaceutically acceptable derivatives thereof.

Before the introduction of antibiotics, patients suffering from acute microbial infections (e.g. tuberculosis or pneumonia) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria. Indeed, more than 70% of bacteria that give rise to hospital acquired infections in the USA resist at least one of the main antimicrobial agents that are typically used to fight infection (*Nature Reviews, Drug Discovery* 1, 895-910 (2002)).

One way of tackling the growing problem of resistant bacteria is the development of new classes of antimicrobial agents. However, until the introduction of linezolid in 2000, there had been no new class of antibiotic marketed for over 37 years. Moreover, even the development of new classes of antibiotic provides only a temporary solution, and indeed there are already reports of resistance of certain bacteria to linezolid (*Lancet* 357, 1179 (2001) and *Lancet* 358, 207-208 (2001)).

In order to develop more long-term solutions to the problem of bacterial resistance, it is clear that alternative approaches are required. One such alternative approach is to minimise, as much as is possible, the opportunities that bacteria are given for developing resistance to important antibiotics. Thus, strategies that can be adopted include limiting the use of antibiotics for the treatment of non-acute infections, as well as controlling which antibiotics are fed to animals in order to promote growth.

However, in order to tackle the problem more effectively, it is necessary to gain an understanding of the actual mechanisms by which bacteria generate resistance to antibiotic agents. To do this requires first a consideration of how current antibiotic agents work to kill bacteria.

Antimicrobial agents target essential components of bacterial metabolism. For example, the β-lactams (e.g. penicillins and cephalosporins) inhibit cell wall synthesis, whereas other agents inhibit a diverse range of targets, such as DNA gyrase (quinolones) and protein synthesis (e.g. macrolides, aminoglycosides, tetracyclines and oxazolidinones). The range of organisms against which the antimicrobial agents are effective varies, depending upon which organisms are heavily reliant upon the metabolic step(s) that is/are inhibited. Further, the effect upon bacteria can vary from a mere inhibition of growth (i.e. a bacteriostatic effect, as seen with agents such as the tetracyclines) to full killing (i.e. a bactericidal effect, as seen, e.g. with penicillin).

Bacteria have been growing on Earth for more than 3 billion years and, in that time, have needed to respond to vast numbers of environmental stresses. It is therefore perhaps not surprising that bacteria have developed a seemingly inexhaustible variety of mechanisms by which they can respond to the metabolic stresses imposed upon them by antibiotic agents. Indeed, mechanisms by which the bacteria can generate resistance include strategies as diverse as inactivation of the drug, modification of the site of action, modification of the permeability of the cell wall, overproduction of the target enzyme and bypass of the inhibited steps. Nevertheless, the rate of resistance emerges to a particular agent has been observed to vary widely, depending upon factors such as the agent's mechanism of action, whether the agent's mode of killing is time- or concentration-dependent, the potency against the population of bacteria and the magnitude and duration of the available serum concentration.

It has been proposed (*Science* 264, 388-393 (1994)) that agents that target single enzymes (e.g. rifampicin) are the most prone to the development of resistance. Further, the longer that suboptimal levels of antimicrobial agent are in contact with the bacteria, the more likely the emergence of resistance.

Moreover, it is now known that many microbial infections include sub-populations of bacteria that are phenotypically resistant to antimicrobials (*J. Antimicrob. Chemother.* 4, 395-404 (1988); *J. Med. Microbiol.* 38, 197-202 (1993); *J. Bacteriol.* 182, 1794-1801 (2000); *ibid.* 182, 6358-6365 (2000); *ibid.* 183, 6746-6751 (2001); *FEMS Microbiol. Lett.* 202, 59-65 (2001); and *Trends in Microbiology* 13, 34-40 (2005)). There appear to be several types of such phenotypically resistant bacteria, including persisters, stationary-phase bacteria, as well as those in the depths of biofilms. However, each of these types is characterised by its low rate of growth compared to log-phase bacteria under the same conditions. Nutritional starvation and high cell densities are also common characteristics of such bacteria.

Although resistant to antimicrobial agents in their slow-growing state, phenotypically resistant bacteria differ from those that are genotypically resistant in that they regain their susceptibility to antimicrobials when they return to a fast-growing state (e.g. when nutrients become more readily available to them).

The presence of phenotypically resistant bacteria in an infection leads to the need for prolonged courses of antimicrobial agents, comprising multiple doses. This is because the resistant, slowly multiplying bacteria provide a pool of "latent" organisms that can convert to a fast-growing state when the conditions allow (thereby effectively re-initiating the infection). Multiple doses over time deal with this issue by gradually killing off the "latent" bacteria that convert to "active" form.

However, dealing with "latent" bacteria by administering prolonged courses of antimicrobials poses its own problems. That is, prolonged exposure of bacteria to suboptimal concentrations of antimicrobial agent can lead to the emergence of genotypically resistant bacteria, which can then multiply rapidly in the presence of even high concentrations of the antimicrobial.

Long courses of antimicrobials are more likely to encourage the emergence of genotypic resistance than shorter courses on the grounds that non-multiplying bacterial will tend to survive and, interestingly, probably have an enhanced ability to mutate to resistance (*Proc. Natl. Acad.*

Sci. USA 92, 11736-11740 (1995); *J. Bacteriol.* 179, 6688-6691 (1997); and *Antimicrob. Agents Chemother.* 44, 1771-1777 (2000)).

In the light of the above, a new approach to combating the problem of bacterial resistance might be to select and develop antimicrobial agents on the basis of their ability to kill "latent" microorganisms. The production of such agents would allow, amongst other things, for the shortening of chemotherapy regimes in the treatment of microbial infections, thus reducing the frequency with which genotypical resistance arises in microorganisms.

International Patent Application, Publication Number WO2000028074 describes a method of screening compounds to determine their ability to kill clinically latent microorganisms. Using this method, the Applicant has observed that many conventional antimicrobial agents, such as neomycin and mupirocin, which otherwise exhibit excellent biological activity against log phase (i.e. multiplying) bacteria, exhibit little or no activity against clinically latent microorganisms. This observation has necessitated the development of novel antimicrobials which may be used to kill clinically latent microorganisms.

International Patent Application, Publication Numbers WO2007054693, WO2008117079 and WO2008142384 describe compounds which exhibit biological activity against clinically latent microorganisms. Examples of such compounds include 4-methyl-8-phenoxy-1-(2-phenylethyl)-2,3-dihydro-1H-pyrrolo[3,2-c]quinoline, 4-(3-benzylpyrrolidin-1-yl)-2-methyl-6-phenoxyquinoline, N-[4-(3-benzylpyrrolidin-1-yl)-2-methylquinolin-6-yl]benzamide and pharmaceutically acceptable derivatives thereof.

Mupirocin is an antibiotic originally isolated from *Pseudomonas fluorescens*. Mupirocin acts as a potent inhibitor of bacterial protein and RNA synthesis by inhibition of isoleucyl-transfer RNA synthase. It is known to be effective against a wide variety of bacteria including *Staphylococcus aureus*, including methicillin-resistant strains, and Gram-negative organisms such as *Escherichia coli* and *Haemophilus influenzae*.

Mupirocin is commercially available in Europe under the trade name Bactroban® in cream and ointment form. Bactroban® is indicated for the treatment of skin infections such as impetigo, folliculitis and furunculosis. It is also indicated for the eradication of *S. aureus* from the anterior nares, where it is located in about 20% of people and decolonisation of the nose for MRSA. Removal of *S. aureus* from the nose in hospital inpatients is associated with a decrease in the incidence of surgical site (Bode et al., *N. Engl. J. Med.*, 362(1), 9-17, (2010)) and nosocomial (Perl et al., *N. Engl. J. Med.*, 346(24), 1871-1877, (2002)) infections.

The antibacterial activity of mupirocin in combination with certain other antibiotics has been reported previously. For example, Ghiselli et al. (*J. Surg. Res.*, 99(2), 316-320, (2001)) have studied the effect of mupirocin in combination with amoxicillin-clavulate, which produced complete suppression of growth of *S. aureus* and MRSA in a rat model of the prevention of vascular prosthetic graft infections. In addition, Alou et al. (*J. Antimicrob. Agents*, 23(5), 513-516, (2004)) observed a 2.5 $\log_{10}$ CFU/ml reduction for a $10^6$ CFU/ml inoculum of *S. aureus* for a combination of mupirocin and amoxicillin-clavulate.

International Patent Application Publication No. WO2012017215 discloses a combination comprising 4-methyl-8-phenoxy-1-(2-phenylethyl)-2,3-dihydro-1H-pyrrolo[3,2-c]quinoline or a pharmaceutically acceptable derivative thereof and another antimicrobial agent selected from the group consisting of a beta-lactam antimicrobial agent, mupirocin and chlorhexidine or a pharmaceutically acceptable derivative thereof.

Neomycin is commercially available in Europe in combination with chlorhexidine under the trade name Naseptin® in the form of a nasal cream. Naseptin® is indicated for the eradication of nasal infection with, and carriage of, Staphylococci. Neomycin is also available commercially in Europe under the trade name Nivemycin® in tablet form. Nivemycin® includes neomycin as its sulfate salt and is indicated for pre-operative sterilisation of the bowel. It is also indicated as being useful in the treatment of impending hepatic coma, including portal systemic encephalopathy.

International Patent Application Publication No. WO2012017216 discloses a combination comprising 4-methyl-8-phenoxy-1-(2-phenylethyl)-2,3-dihydro-1H-pyrrolo[3,2-c]quinoline or a pharmaceutically acceptable derivative thereof and an aminoglycoside antimicrobial agent (such as neomycin) or a pharmaceutically acceptable derivative thereof.

The present invention is based upon the unexpected finding that the antimicrobial activity of certain antimicrobial agents, in particular mupirocin and neomycin or pharmaceutically acceptable derivatives thereof, is substantially improved when these agents are administered as a triple combination with the compound 4-methyl-8-phenoxy-1-(2-phenylethyl)-2,3-dihydro-1H-pyrrolo[3,2-c]quinoline or a pharmaceutically acceptable derivative thereof.

The present invention is further based upon the finding that this improvement in antimicrobial activity is seen with a low concentration of the compound 4-methyl-8-phenoxy-1-(2-phenylethyl)-2,3-dihydro-1H-pyrrolo[3,2-c]quinoline or a pharmaceutically acceptable derivative thereof.

Moreover, this triple combination of active agents has surprisingly been shown to exhibit synergistic antimicrobial activity against log phase (i.e. multiplying) and stationary phase (i.e. non-multiplying) microorganisms, i.e. greater than the expected additive effect of each agent at the stated dosage level. The surprising biological activity of the combination of the present invention offers the opportunity to shorten chemotherapy regimes and may result in a reduction in the emergence of microbial resistance associated with the use of such combinations.

Synergy in the context of antimicrobial drugs is measured in a number of ways that conform to the generally accepted opinion that "synergy is an effect greater than additive". One of the ways to assess whether synergy has been observed is to use the "chequerboard" technique. This is a well-accepted method that leads to the generation of a value called the fractional inhibitory concentration index (FICI). Orhan et al J. Clin. Microbiol. 2005, 43(1):140 describes the chequerboard method and analysis in the paragraph bridging pages 140-141, and explains that the FICI value is a ratio of the sum of the MIC (Minimum Inhibitory Concentration) level of each individual component alone and in the mixture. The combination is considered synergistic when the ΣFIC is <0.5, indifferent when the ΣFIC is >0.5 to <2, and antagonistic when the ΣFIC is >2.

Another accepted test for ascertaining the presence or absence of synergy is to use time-kill methods where the dynamic effect of a drug combination is compared to each drug alone when assessing the effect on bacterial log or stationary-growth over time. Again, the possible results are for synergistic, additive or antagonistic effects.

Thus, in one embodiment the present invention provides 4-methyl-8-phenoxy-1-(2-phenylethyl)-2,3-dihydro-1H-pyrrolo[3,2-c]quinoline or a pharmaceutically acceptable derivative thereof in combination with mupirocin and neomycin or pharmaceutically acceptable derivatives thereof.

In a further embodiment, the present invention provides a combination comprising 4-methyl-8-phenoxy-1-(2-phenylethyl)-2,3-dihydro-1H-pyrrolo[3,2-c]quinoline or a pharmaceutically acceptable derivative thereof, mupirocin or a pharmaceutically acceptable derivative thereof and neomycin or a pharmaceutically acceptable derivative thereof.

In another embodiment, the present invention provides the use of 4-methyl-8-phenoxy-1-(2-phenylethyl)-2,3-dihydro-1H-pyrrolo[3,2-c]quinoline or a pharmaceutically acceptable derivative thereof in combination with mupirocin or a pharmaceutically acceptable derivative thereof and neomycin or a pharmaceutically acceptable derivative thereof for the manufacture of a medicament for the prevention and/or treatment of a microbial infection; in particular for killing multiplying, non-multiplying and/or clinically latent microorganisms associated with such an infection.

The invention further provides a method of preventing or treating a microbial infection, in particular killing multiplying, non-multiplying and/or clinically latent microorganisms associated with such an infection, which comprises administering to a mammal, including man, 4-methyl-8-phenoxy-1-(2-phenylethyl)-2,3-dihydro-1H-pyrrolo[3,2-c]quinoline or a pharmaceutically acceptable derivative thereof in combination with mupirocin or a pharmaceutically acceptable derivative thereof and neomycin or a pharmaceutically acceptable derivative thereof.

In another embodiment, the invention provides the use of 4-methyl-8-phenoxy-1-(2-phenylethyl)-2,3-dihydro-1H-pyrrolo[3,2-c]quinoline or a pharmaceutically acceptable derivative thereof in combination with mupirocin or a pharmaceutically acceptable derivative thereof and neomycin or a pharmaceutically acceptable derivative thereof for the prevention and/or treatment of a microbial infection; in particular for killing multiplying, non-multiplying and/or clinically latent microorganisms associated with such an infection.

As used herein, the terms "combination" and "in combination with" refer to both separate and sequential administration of 4-methyl-8-phenoxy-1-(2-phenylethyl)-2,3-dihydro-1H-pyrrolo[3,2-c]quinoline or a pharmaceutically acceptable derivative thereof and mupirocin or a pharmaceutically acceptable derivative thereof and neomycin or a pharmaceutically acceptable derivative thereof. When the agents are administered sequentially, either 4-methyl-8-phenoxy-1-(2-phenylethyl)-2,3-dihydro-1H-pyrrolo[3,2-c] quinoline or a pharmaceutically acceptable derivative thereof, or mupirocin or a pharmaceutically acceptable derivative thereof, or neomycin or a pharmaceutically acceptable derivative thereof may be administered first. When administration is simultaneous, the agents may be administered either in the same or a different pharmaceutical composition. Adjunctive therapy, i.e. where one or two agent(s) are used as the primary treatment and the other agent is used to assist that primary treatment, is also an embodiment of the present invention.

According to a further embodiment of the invention, there is provided a product comprising 4-methyl-8-phenoxy-1-(2-phenylethyl)-2,3-dihydro-1H-pyrrolo[3,2-c]quinoline or a pharmaceutically acceptable derivative thereof and mupirocin or a pharmaceutically acceptable derivative thereof and neomycin or a pharmaceutically acceptable derivative thereof as a combined preparation for simultaneous, separate or sequential use in the prevention and/or treatment of a microbial infection.

There is also provided a pharmaceutical composition comprising 4-methyl-8-phenoxy-1-(2-phenylethyl)-2,3-dihydro-1H-pyrrolo[3,2-c]quinoline or a pharmaceutically acceptable derivative thereof, mupirocin or a pharmaceutically acceptable derivative thereof and neomycin or a pharmaceutically acceptable derivative thereof, and a pharmaceutically acceptable adjuvant, diluent or carrier. Such a composition may be used for the prevention and/or treatment of microbial infections, and in particular for use in killing multiplying, non-multiplying and/or clinically latent microorganisms associated with a microbial infection.

The combinations of the present invention may be used to prevent and/or treat microbial infections. In particular they may be used to kill multiplying, non-multiplying and/or clinically latent microorganisms associated with microbial infections. References herein to the treatment of a microbial infection therefore include killing multiplying, non-multiplying and/or clinically latent microorganisms associated with such infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or
(II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*);

Streptococci (e.g. beta-haemolytic, pyogenic streptococci (such as *Strept. agalactiae, Strept. canis, Strept. dysgalactiae dysgalactiae, Strept dysgalactiae equisimilis, Strept. equi equi, Strept equi zooepidemicus, Strept. iniae, Strept. porcinus* and *Strept. pyogenes*), microaerophilic, pyogenic streptococci (*Streptococcus* "milleri", such as *Strept. anginosus, Strept. constellatus constellatus, Strept. constellatus pharyngidis* and *Strept. intermedius*), oral streptococci of the "mitis" (alpha-haemolytic—*Streptococcus* "viridans", such as *Strept mitis, Strept. oralis, Strept. sanguinis, Strept. cristatus, Strept. gordonii* and *Strept. parasanguinis*), "salivarius" (non-haemolytic, such as *Strept. salivarius* and *Strept. vestibularis*) and "mutans" (tooth-surface streptococci, such as *Strept. criceti, Strept. mutans, Strept. ratti* and *Strept sobrinus*) groups, *Strept. acidominimus, Strept bovis, Strept. faecalis, Strept. equinus, Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*;

Bacillaceae, such as *Bacillus anthracis, Bacillus subtilis, Bacillus thuringiensis, Bacillus stearothermophilus* and *Bacillus cereus*;

Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia alvei*), *Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonnei*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*);

Enterococci (e.g. *Enterococcus avium, Enterococcus caseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*);

*Helicobacter* (e.g. *Helicobacter pylori, Helicobacter cinaedi* and *Helicobacter fenneliae*);

*Acinetobacter* (e.g. *A. baumanii, A. calcoaceticus, A. haemolyticus, A. johnsonii, A. junii, A. woffi* and *A. radioresistens*);

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*);

*Bacteroides fragilis*;

*Peptococcus* (e.g. *Peptococcus niger*);

*Peptostreptococcus*;

*Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. carnis, C. celatum, C. clostridioforme, C. cochlearium, C. cocleatum, C. fallax, C. ghonii, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*);

*Mycoplasma* (e.g. *M. pneumoniae, M. hominis, M. genitalium* and *M. urealyticum*);

Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum, Mycobacterium chubense, Mycobacterium confluentis, Mycobacterium conspicuum, Mycobacterium cookii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*);

*Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*);

*Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*);

*Actinomyces* (e.g. *Actinomyces israelii*);

*Brucella* (e.g. *Brucella abortus, Brucella canis, Brucella melintensis* and *Brucella suis*);

*Campylobacter* (e.g. *Campylobacter jejuni, Campylobacter coli, Campylobacter lari* and *Campylobacter fetus*);

*Listeria monocytogenes*;

*Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*);

*Erysipelothrix rhusopathiae*;
Corynebacteriaceae (e.g. *Corynebacterium diphtheriae, Corynebacterium jeikeum* and *Corynebacterium urealyticum*);
Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);
*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);
*Bordetella* (e.g. *Bordetella bronchiseptica, Bordetella hinzii, Bordetella holmseii, Bordetella parapertussis, Bordetella pertussis* and *Bordetella trematum*);
Nocardiaceae, such as *Nocardia* (e.g. *Nocardia asteroides* and *Nocardia brasiliensis*);
*Rickettsia* (e.g. *Ricksettsii* or *Coxiella burnetii*);
*Legionella* (e.g. *Legionalla anisa, Legionalla birminghamensis, Legionalla bozemanii, Legionalla cincinnatiensis, Legionalla dumoffii, Legionalla feeleii, Legionalla gormanii, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*);
*Moraxella catarrhalis*;
*Cyclospora cayetanensis*;
*Entamoeba histolytica*;
*Giardia lamblia*;
*Trichomonas vaginalis*;
*Toxoplasma gondii*;
*Stenotrophomonas maltophilia*;
*Burkholderia cepacia*; *Burkholderia mallei* and *Burkholderia pseudomallei*;
*Francisella tularensis*;
*Gardnerella* (e.g. *Gardneralla vaginalis* and *Gardneralla mobiluncus*);
*Streptobacillus moniliformis*;
Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);
*Bartonella* (*Bartonella bacilliformis, Bartonella clarridgeiae, Bartonella elizabethae, Bartonella henselae, Bartonella quintana* and *Bartonella vinsonii arupensis*);
*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);
*Spirillium* (e.g. *Spirillum minus*);
*Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);
*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*);
*Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);
*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);
*Chlamydia* (e.g. *Chlamydia trachomatis*);
*Cryptosporidium* (e.g. *C. parvum, C. hominis, C. canis, C. felis, C. meleagridis* and *C. muris*);
*Chlamydophila* (e.g. *Chlamydophila abortus* (*Chlamydia psittaci*), *Chlamrydophila pneumoniae* (*Chlamydia pneumoniae*) and *Chlamydophila psittaci* (*Chlamydia psittaci*));
*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);
*Gemella* (e.g. *Gemella bergeri, Gemella haemolysans, Gemella morbillorum* and *Gemella sanguinis*); and
*Ureaplasma* (e.g. *Ureaplasma parvum* and *Ureaplasma urealyticum*).

As used herein, the term "fungi" (and derivatives thereof, such as "fungal infection") includes, but is not limited to, references to organisms (or infections due to organisms) of the following classes and specific types:
*Absidia* (e.g. *Absidia corymbifera*);
*Ajellomyces* (e.g. *Ajellomyces capsulatus* and *Ajellomyces dermatitidis*);
*Arthroderma* (e.g. *Arthroderma benhamiae, Arthroderma fulvum, Arthroderma gypseum, Arthroderma incurvatum, Arthroderma otae* and *Arthroderma vanbreuseghemii*);
*Aspergillus* (e.g. *Aspergillus flavus, Aspergillus fumigatus* and *Aspergillus niger*);
*Blastomyces* (e.g. *Blastomyces dermatitidis*);
*Candida* (e.g. *Candida albicans, Candida glabrata, Candida guilliermondii, Candida krusei, Candida parapsilosis, Candida tropicalis* and *Candida pelliculosa*);
*Cladophialophora* (e.g. *Cladophialophora carrionii*);
*Coccidioides* (e.g. *Coccidioides immitis* and *Coccidioides posadasii*);
*Cryptococcus* (e.g. *Cryptococcus neoformans*);
*Cunninghamella* (e.g. *Cunninghamella* sp.)
*Epidermophyton* (e.g. *Epidermophyton floccosum*);
*Exophiala* (e.g. *Exophiala dermatitidis*);
*Filobasidiella* (e.g. *Filobasidiella neoformans*);
*Fonsecaea* (e.g. *Fonsecaea pedrosoi*);
*Fusarium* (e.g. *Fusarium solani*);
*Geotrichum* (e.g. *Geotrichum candidum*);
*Histoplasma* (e.g. *Histoplasma capsulatum*);
*Hortaea* (e.g. *Hortaea wernecki*);

*Issatschenkia* (e.g. *Issatschenkia orientalis*);
*Madurella* (e.g. *Madurella grisae*);
*Malassezia* (e.g. *Malassezia furfur, Malassezia globosa, Malassezia obtusa, Malassezia pachydermatis, Malassezia restricta, Malassezia slooffiae* and *Malassezia sympodialis*);
*Microsporum* (e.g. *Microsporum canis, Microsporum fulvum* and *Microsporum gypseum*);
*Microsporidia;*
*Mucor* (e.g. *Mucor circinelloides*);
*Nectria* (e.g. *Nectria haematococca*);
*Paecilomyces* (e.g. *Paecilomyces variotii*);
*Paracoccidioides* (e.g. *Paracoccidioides brasiliensis*);
*Penicillium* (e.g. *Penicillium marneffei*);
*Pichia* (e.g. *Pichia anomala* and *Pichia guilliermondii*);
*Pneumocystis* (e.g. *Pneumocystis jiroveci* (*Pneumocystis carinii*));
*Pseudallescheria* (e.g. *Pseudallescheria boydii*);
*Rhizopus* (e.g. *Rhizopus oryzae*);
*Rhodotorula* (e.g. *Rhodotorula rubra*);
*Scedosporium* (e.g. *Scedosporium apiospermum*);
*Schizophyllum* (e.g. *Schizophyllum commune*);
*Sporothrix* (e.g. *Sporothrix schenckii*);
*Trichophyton* (e.g. *Trichophyton mentagrophytes, Trichophyton rubrum, Trichophyton verrucosum* and *Trichophyton violaceum*); and
*Trichosporon* (e.g. *Trichosporon asahii, Trichosporon cutaneum, Trichosporon inkin* and *Trichosporon mucoides*).

Particular bacteria that may treated using a combination of the invention include:
Staphylococci, such as *Staph. aureus* (either Methicillin-sensitive (i.e. MSSA) or Methicillin-resistant (i.e. MRSA)) and *Staph. epidermidis;*
Streptococci, such as *Strept. agalactiae* and *Strept. pyogenes;*
Bacillaceae, such as *Bacillus anthracis;*
Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*);
*Haemophilus influenzae;*
Enterococci, such as *Enterococcus faecalis* and *Enterococcus faecium;* and
Mycobacteria, such as *Mycobacterium tuberculosis.*

Preferably, the bacterium is *S. aureus;* either MSSA or MRSA.

Particular fungi that may be treated with a combination of the invention include *Aspergillus fumigatus, Candida albicans, Cryptococcus neoformans, Histoplasma capsulatum* and *Pneumocystis jiroveci.*

The combinations of the present invention may be used to prevent and/or to treat infections associated with any bacterial or fungal organisms, such as those mentioned above; in particular, they may be used for killing multiplying, non-multiplying and/or clinically latent microorganisms associated with such an infection.

Particular conditions which may be prevented and/or treated using the combinations of the present invention include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne vulgaris, actinomycosis, asthma, bacilliary dysentry, bacterial conjunctivitis, bacterial keratitis, bacterial vaginosis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, eczema, empymea, endocarditis, endometritis, enteric fever, enteritis, epididymitis, epiglottitis, erysipelis, erysipclas, erysipeloid, erythrasma, eye infections, furuncles, *gardnerella* vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, ricin poisoning, Ritter's disease, salmonellosis, salpingitis, septic arthritis, septic infections, septicameia, sinusitis, skin infections (e.g. skin granulomas, impetigo, folliculitis and furunculosis), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, favus, histoplasmosis, intertrigo, mucormycosis, tinea (e.g. tinea corporis, tinea *capitis*, tinea cruris, tinea pedis and tinea unguium), onychomycosis, pityriasis versicolor, ringworm and sporotrichosis; or infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilus influenzae, Enterococcus faecalis* and *Enterococcus faecium.*

References herein to "treatment" extend to prophylaxis as well as the treatment of established diseases or symptoms.

It will be appreciated that in one aspect of the present invention one or more additional antimicrobial compounds may also be administered with the above-mentioned combinations of the invention.

As used herein the term "pharmaceutically acceptable derivative" means:
(a) pharmaceutically acceptable salts; and/or
(b) solvates (including hydrates).

Suitable acid addition salts include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts, and the like.

A preferred salt of mupirocin is the calcium salt thereof, i.e. mupirocin calcium.

A preferred salt of neomycin is the sulfate salt thereof, i.e. neomycin sulfate.

For the avoidance of doubt, references herein to 4-methyl-8-phenoxy-1-(2-phenylethyl)-2,3-dihydro-1H-pyrrolo[3,2-c]quinoline mean a compound having the following chemical structure:

4-methyl-8-phenoxy-1-(2-phenylethyl)-2,3-dihydro-1H-pyrrolo[3,2-c]quinoline or a pharmaceutically acceptable derivative thereof may be prepared by methods known in the art, for example by following the methods disclosed in International Patent Application, Publication Numbers WO2007054693 and WO2008056151. Preferred pharmaceutically acceptable derivatives of 4-methyl-8-phenoxy-1-(2-phenylethyl)-2,3-dihydro-1H-pyrrolo[3,2-c]quinoline include the hydrochloride and mesylate salts thereof.

Mupirocin and mupirocin calcium are commercially available, for example from Sigma Aldrich Limited. Mupirocin is also known under the brand name Bactroban® which is available in the form of an ointment or a cream, specifically as a nasal ointment.

Neomycin and neomycin sulfate are commercially available, for example from Sigma Aldrich Limited. Neomycin is also known under the brand name Nivemycin® in the form of tablets. When combined with chlorhexidine dihydrochloride, the combination is known under the brand name Naseptin® in the form of a nasal cream.

The compounds of the invention may be administered simultaneously or sequentially. When administered sequentially, 4-methyl-8-phenoxy-1-(2-phenylethyl)-2,3-dihydro-1H-pyrrolo[3,2-c]quinoline or a pharmaceutically acceptable derivative thereof or mupirocin or a pharmaceutically acceptable derivative thereof, or neomycin or a pharmaceutically acceptable derivative thereof, may be administered first. When administration is simultaneous, the combination may be administered either in the same or a different pharmaceutical composition.

The compounds of the invention may be administered as the raw material but the active ingredients are preferably provided in the form of pharmaceutical compositions.

The active ingredients may be used either as separate formulations or as a single combined formulation. When combined in the same formulation it will be appreciated that the compounds must be stable and compatible with each other and the other components of the formulation.

Formulations of the invention include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration. The most suitable route of administration may depend upon the condition and disorder of the patient.

Preferably, the compositions of the invention are formulated for oral, topical or inhaled administration.

The formulations may conveniently be presented in unit dosage form and may be prepared by any of the methods well known in the art of pharmacy e.g. as described in "*Remington: The Science and Practice of Pharmacy*", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% for liquid preparations.

A suitable concentration for mupirocin or a pharmaceutically acceptable derivative thereof is from about 0.2 to 2% by weight of the total combination. For example 0.2, 0.25, 0.3, 0.4, 0.5, 0.6, 0.7, 0.75, 0.8, 0.9, 1, 1.1, 1.2, 1.3, 1.4, 1.5, 1.6, 1.7, 1.8, 1.9 or 2%, preferably about 2% by weight of the total combination.

A suitable concentration for neomycin or a pharmaceutically acceptable derivative thereof is from about 0.05 to 1%, for example 0.05, 0.06, 0.07, 0.08, 0.09, 0.1, 0.2, 0.25, 0.3, 0.4, 0.5, 0.6, 0.7, 0.75, 0.8, 0.9 or 1% preferably from about 0.05 to 0.5%, e.g. about 0.5% by weight of the total combination.

Surprisingly it has been found that the triple combination has synergistic antimicrobial activity even with a low concentration of 4-methyl-8-phenoxy-1-(2-phenylethyl)-2,3-dihydro-1H-pyrrolo[3,2-c]quinoline or a pharmaceutically acceptable derivative thereof. It has also surprisingly been found that the triple combination is effective with low concentrations of mupirocin or a pharmaceutically acceptable derivative thereof, and/or neomycin or a pharmaceutically acceptable derivative thereof.

A suitable concentration for 4-methyl-8-phenoxy-1-(2-phenylethyl)-2,3-dihydro-1H-pyrrolo[3,2-c]quinoline or a pharmaceutically acceptable derivative thereof is from about 0.01 to about 2%, preferably 0.1 to about 1%, for example 0.1, 0.2, 0.25, 0.3, 0.4, 0.5, 0.6, 0.7, 0.75, 0.8, 0.9, or 1% by weight of the total combination. Preferably about 1% by weight of the total combination.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or moulding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Moulded tablets may be made by moulding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use. Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Topical compositions, which are useful for treating disorders of the skin or of membranes accessible by digitation (such as membrane of the mouth, vagina, cervix, anus and rectum), include creams, ointments, lotions, sprays, gels and sterile aqueous solutions or suspensions. As such, topical compositions include those in which the active ingredients are dissolved or dispersed in a dermatological vehicle known in the art (e.g. aqueous or non-aqueous gels, ointments, water-in-oil or oil-in-water emulsions). Constituents of such vehicles may comprise water, aqueous buffer solutions, non-aqueous solvents (such as ethanol, isopropanol, benzyl alcohol, 2-(2-ethoxyethoxy)ethanol, propylene glycol, propylene glycol monolaurate, glycofurol or glycerol), oils (e.g. a mineral oil such as a liquid paraffin, natural or synthetic triglycerides such as Miglyol™, or silicone oils such as dimethicone). Depending, inter alia, upon the nature of the formulation as well as its intended use and site of application, the dermatological vehicle employed may contain one or more components selected from the following list: a solubilising agent or solvent (e.g. a β-cyclodextrin, such as hydroxypropyl β-cyclodextrin, or an alcohol or polyol such as ethanol, propylene glycol or glycerol); a thickening agent (e.g. hydroxymethyl cellulose, hydroxypropyl cellulose, carboxymethyl cellulose or carbomer); a gelling agent (e.g. a polyoxyethylene-polyoxypropylene copolymer); a preservative (e.g. benzyl alcohol, benzalkonium chloride, chlorhexidine, chlorbutol, a benzoate, potassium sorbate or EDTA or salt thereof); and pH buffering agent(s) (e.g. a mixture of dihydrogen phosphate and hydrogen phosphate salts, or a mixture of citric acid and a hydrogen phosphate salt). Topical formulations may also be formulated as a transdermal patch.

Methods of producing topical pharmaceutical compositions such as creams, ointments, lotions, sprays and sterile aqueous solutions or suspensions are well known in the art. Suitable methods of preparing topical pharmaceutical compositions are described, e.g. in WO9510999, U.S. Pat. No. 6,974,585, WO2006048747, as well as in documents cited in any of these references.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria, fungi described above, (e.g. any of the *Staphylococci*, *Streptococci*, *Mycobacteria* or *Pseudomonas* organisms mentioned hereinbefore, such as *S. aureus* (e.g. Methicillin resistant *S. aureus* (MRSA))). In a preferred embodiment of the invention, there is provided a topical pharmaceutical composition for the nasal decolonisation of MRSA.

Topical compositions of the invention may be used for pre-operative surgical hand disinfection, antiseptic handwashing, and pre- and post-operative antisepsis for patients undergoing elective surgery.

Particular bacterial conditions that may be treated by topical pharmaceutical compositions of the present invention also include the skin- and membrane-related conditions disclosed hereinbefore, as well as: acne vulgaris; rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal peri-anal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii*, *M. malmoense*, *M. szulgai*, *M. simiae*, *M. gordonae*, *M. haemophilum*, *M. avium*, *M. intracellulare*, *M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

Particular fungal conditions that may be treated by topical pharmaceutical compositions of the present invention also include the skin and membrane-related conditions disclosed hereinbefore, as well as: candidiasis; sporotrichosis; ringworm (e.g. tinea pedis, tinea cruris, tinea *capitis*, tinea unguium or tinea corporis); tinea versicolor; and infections with *Trichophyton*, *Microsporum*, *Epidermophyton* or *Pityrosporum ovale* fungi.

Compositions for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack. Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combinations of the invention by means of a single patient pack, or patients packs of each composition, including a package insert directing the patient to the correct use of the invention is a further feature of this invention.

According to a further embodiment of the present invention there is provided a patient pack comprising at least one active ingredient of the combinations according to the invention, i.e. at least one of 4-methyl-8-phenoxy-1-(2-phenylethyl)-2,3-dihydro-1H-pyrrolo[3,2-c]quinoline or a pharmaceutically acceptable derivative thereof, mupirocin or a pharmaceutically acceptable derivative thereof, and neomycin or a pharmaceutically acceptable derivative thereof, and an information insert containing directions on the use of the combination of the invention.

In another embodiment of the invention, there is provided a triple pack comprising in association for separate administration, (a) 4-methyl-8-phenoxy-1-(2-phenylethyl)-2,3-dihydro-1H-pyrrolo[3,2-c]quinoline or a pharmaceutically acceptable derivative thereof, (b) mupirocin or a pharmaceutically acceptable derivative thereof, and (c) neomycin or a pharmaceutically acceptable derivative thereof.

The amount of active ingredients required for use in treatment will vary with the nature of the condition being treated and the age and condition of the patient, and will ultimately be at the discretion of the attendant physician or veterinarian. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-does per day.

Biological Tests

Test procedures that may be employed to determine the biological (e.g. bactericidal or antimicrobial) activity of the active ingredients include those known to persons skilled in the art for determining:

(a) bactericidal activity against clinically latent bacteria; and
(b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:

(1) growing a bacterial culture to stationary phase;
(2) treating the stationary phase culture with one or more antimicrobial agents at a concentration and or time sufficient to kill growing bacteria, thereby selecting a phenotypically resistant sub-population;
(3) incubating a sample of the phenotypically resistant subpopulation with one or more test compounds or agents; and
(4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO2005014585, the disclosures of which document are hereby incorporated by reference), of Minimum Inhibitory Concentration (MIC) or Minimum Bactericidal Concentration (MBC) for a test compound. Specific examples of such methods are described below.

EXAMPLES

Materials and Methods

Bacterial Strains and Culture Medium

*Staphylococcus aureus* (Oxford); Gram positive; Reference strain.

Nutrient Broth No. 2 (NB) (Oxoid, Cambridge, UK) was used for overnight growth of bacteria.

Iso-Sensitest Broth (Oxoid) was used for evaluation of efficacy of antimicrobial combinations.

Trypton soya agar (TSA) (Oxoid, Cambridge, UK) was used for growth and quantification of organisms. All media were autoclaved at 121° C. for 15 minutes prior to use.

Bacterial Growth Conditions

Bacterial cultures were prepared by inoculation of 10 ml of nutrient broth with a single colony of bacteria on blood agar or TSA and incubated at 37° C. with continuous shaking at 100 rpm for 16 to 24 hours. The overnight cultures were used for experimental tests.

For CFU counting, the bacterial suspensions were diluted using sterile deionized water or phosphate-buffered saline (PBS, Sigma Aldrich Ltd, Poole, Dorset, UK). 100 µl of 10-fold serial dilutions of bacteria culture were plated on one third of TSA plates in triplicate and incubated 24 to 48 hours at 37° C. The number of cells presented on the plates was counted using an AcoLyte colony counter (Synbiosis) and results were expressed as Colony Forming Units/ml (CFU/ml).

Antibiotics

Mupirocin (in calcium salt form) and neomycin (in sulfate salt form) were purchased from Sigma Aldrich Ltd (Poole, Dorset, UK). 4-methyl-8-phenoxy-1-(2-phenylethyl)-2,3-dihydro-1H-pyrrolo[3,2-c]quinoline (in hydrochloride salt form) was provided by Helperby Therapeutics.

Stocks of 10 mg/ml of each of the antibiotics were prepared by dilution in dimethyl sulfoxide (DMSO) or water respectively. The antibiotic solutions were stored at −20° C.

Example 1

The antimicrobial activity of 4-methyl-8-phenoxy-1-(2-phenylethyl)-2,3-dihydro-1H-pyrrolo[3,2-c]quinoline hydrochloride (HT61 HCl) in combination with mupirocin (mupirocin calcium) and neomycin (neomycin sulfate) against *S. aureus* on pig skin was assessed.

The triple combination formulations were prepared as shown below in Tables 1 and 2.

TABLE 1

| Ingredients | % w/w (F017) | |
|---|---|---|
| | A | B |
| Cetyl alcohol | 7.0 | 7.0 |
| Stearyl alcohol | 7.0 | 7.0 |
| Cetomacrogol 1000 | 4.0 | 4.0 |
| Liquid paraffin | 16.0 | 16.0 |
| Water | 60.0 | 60.5 |
| Mupirocin calcium | 2.0 | 2.0 |
| Neomycin Sulfate | 0.5 | 0.5 |
| Xanthan gum | 0.5 | 0 |
| Benzyl alcohol | 2.0 | 2.0 |
| HT61 HCl | 1.0 | 1.0 |

TABLE 2

| Ingredients | % w/w (F019) |
|---|---|
| Water | 1 |
| Neomycin sulfate | 0.5 |
| Cremophore RH 40 | 3 |
| PEG 400 | 20 |
| PEG 400 | 30 |
| PEG 3350 | 33.8 |
| Mupirocin | 2 |
| Benzyl alcohol | 2 |
| HT61 HCl | 1 |

The efficacy of each of the above formulations F017A, F017B and F019 was assessed against *S. aureus* on pig skin. The *S. aureus* culture was grown overnight according to methods known in the art. The overnight culture was then spread on pig skin: 40 µl of culture was used for 2 cm³ of pig skin. Each of the formulations F017A, F017B and F019 was then applied to the pig skin.

Figure 1:
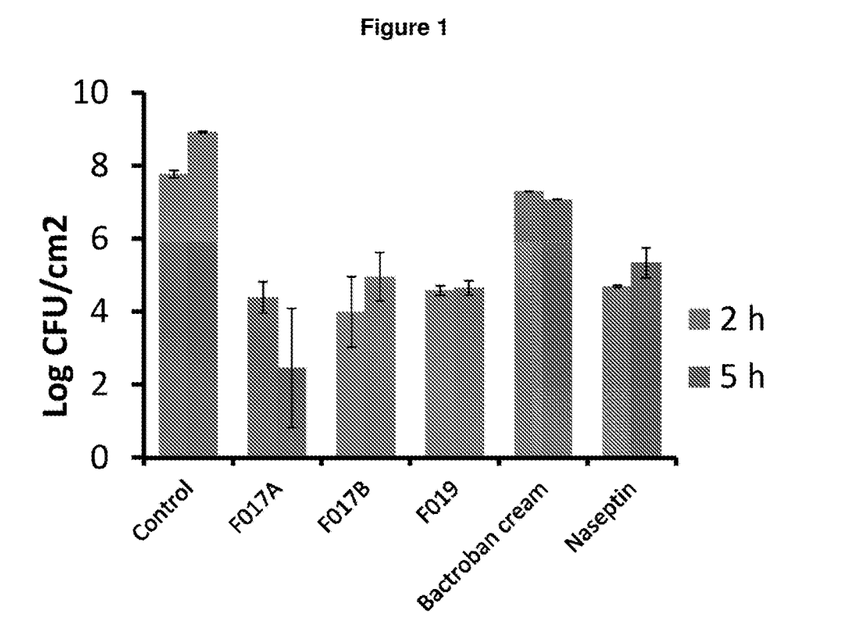

After 2 hours and 5 hours from application of each formulation, the pig skin was swabbed and bacteria on the swab were processed for CFU counting. The results for F017A, F017B and F019 against a control experiment (where no triple combination was applied to the pig skin) and against commercially available products Bactroban® cream (mupirocin) and Naseptin® (chlorhexidine and neomycin) are shown in FIG. 1.

The log kill values for F017A, F017B, F019, Bactroban® cream and Naseptin® are shown in Table 3 below.

TABLE 3

| | Log kill | |
|---|---|---|
| | 2 hour | 5 hour |
| F017A | 3.39 | 6.47 |
| F017B | 3.79 | 3.97 |
| F019 | 3.20 | 4.28 |
| Bactroban cream | 0.47 | 1.84 |
| Naseptin | 3.08 | 3.59 |

It can be seen from Table 3 and FIG. 1 that compared to the control experiment, each of the formulations of the invention: F017A, F017B and F019 demonstrated efficacious antimicrobial activity against *S. aureus* on the pig skin after both 2 hours and 5 hours. F017A showed a particularly high reduction in log CFU after 5 hours with a log kill value of 6.47.

Each of the formulations F017A, F017B and F019 also showed a synergistic improvement in antimicrobial activity compared to mupirocin alone (Bactroban® cream). The Bactroban® cream had a log kill value of 0.47 after 2 hours and 1.84 after 5 hours. In comparison, the formulations of the invention had values of 3.20, 3.39 and 3.79 after 2 hours and 3.97, 4.28 and 6.47 after 5 hours.

Synergistic reductions (in the range of approximately 2.5 log to 4.5 log) in CFU/ml can also be seen in FIG. 1 for all combinations of the invention compared to Bactroban®. The combination of mupirocin with neomycin and HT61 can therefore be seen to synergistically improve the antimicrobial activity of mupirocin alone.

Additionally each of the formulations F017A, F017B and F019 showed an improvement in antimicrobial activity after 5 hours compared to the combination of neomycin and chlorhexidine (Naseptin®). After 5 hours Naseptin® had a log kill value of 3.59 whereas the formulations of the invention had values of 3.97, 4.28 and 6.47.

Example 2

The efficacy of each of the above formulations F017A, F017B and F019 was again assessed against *S. aureus* on pig skin. The *S. aureus* culture was grown overnight according to methods known in the art. The overnight culture was then spread on pig skin: 40 µl of culture was used for 2 cm³ of pig skin. Each of the formulations F017A, F017B and F019 was then applied to the pig skin.

Figure 2:
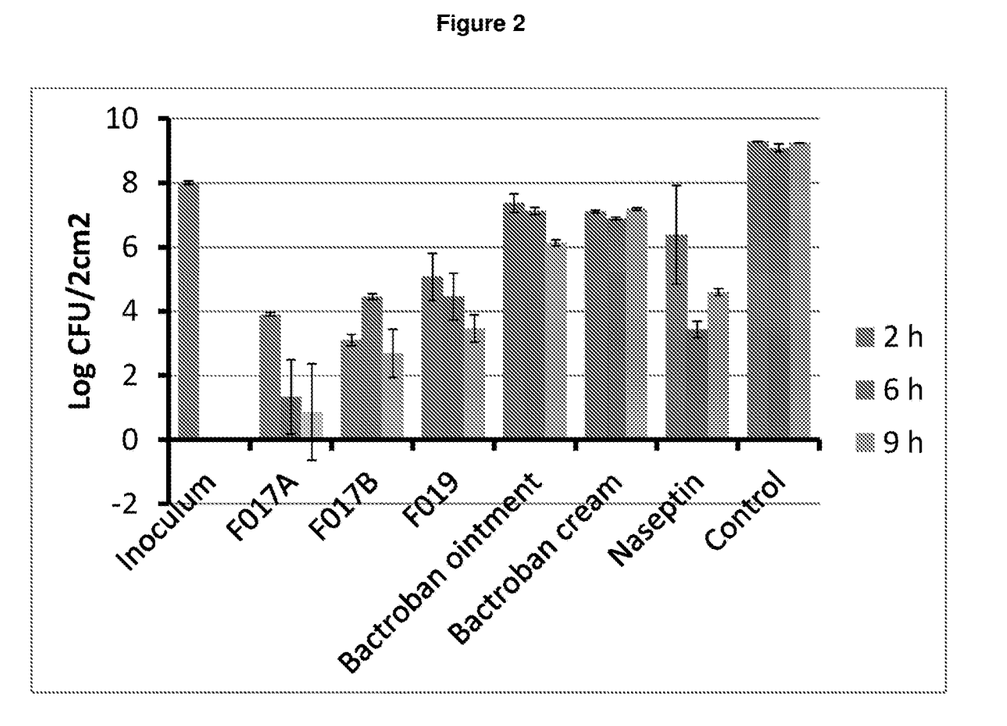

After 2 hours, 6 hours and 9 hours from application of each formulation, the pig skin was swabbed and bacteria on the swab were processed for CFU counting. The results for F017A, F017B and F019 against a control experiment (where no triple combination was applied to the pig skin), an inoculum, and against commercially available products Bactroban® cream (mupirocin), Bactroban® ointment (mupirocin) and Naseptin® (chlorhexidine and neomycin) are shown in FIG. 2.

The log kill values for Example 2 are shown in Table 4 below. The inoculum had a log kill value of 8.

TABLE 4

| | Log kill | | |
|---|---|---|---|
| Formulation | 2 h | 6 h | 9 h |
| F017A | 4.11 | 6.68 | 7.14 |
| F017B | 4.91 | 3.56 | 5.32 |
| F019 | 2.94 | 3.55 | 4.55 |
| Bactroban ointment | 0.63 | 0.88 | 1.87 |
| Bactroban cream | 0.90 | 1.12 | 0.82 |
| Naseptin | 1.63 | 4.58 | 3.42 |

The same trends can be seen from Table 4 and FIG. 2 as in Example 1, namely that the formulations of the invention: F017A, F017B and F019 have synergistically improved antimicrobial activity compared to mupirocin alone. This synergistic improvement is seen for both the ointment and cream form of Bactroban®. F017A in particular exhibits a log kill value of 7.14 after 9 hours compared to values of 1.87 and 0.82 for the Bactroban® ointment and cream respectively.

The formulations of the invention also exhibit significantly longer-lasting antimicrobial activity compared to Naseptin®. From the figures in Table 4 and the plot of FIG. 2 it can be seen that Naseptin® is less effective after 6 hours: the log kill value decreases from 4.58 at 6 hours to 3.42 at 9 hours. In contrast, the formulations of the invention are still effective after 6 hours. Each of F017A, F017B and F019 shows an increase in log kill between 6 hours and 9 hours, with F017A approaching complete kill of S. aureus on the pig skin.

The combination of mupirocin with neomycin and HT61 can therefore be seen to have synergistic and long term antimicrobial activity.

Example 3

The antimicrobial activity of 4-methyl-8-phenoxy-1-(2-phenylethyl)-2,3-dihydro-1H-pyrrolo[3,2-c]quinoline hydrochloride (HT61 HCl) in combination with mupirocin (mupirocin calcium) and neomycin (neomycin sulfate) against S. aureus on pig skin was again assessed.

The triple combination formulations were prepared as shown below in Table 5.

TABLE 5

| Ingredients | F017A All three drugs | % w/w (F022) | | | | | | |
|---|---|---|---|---|---|---|---|---|
| | | A Placebo | B Only Mupirocin | C Only HT61 | D Only Neomycin | E Mupirocin + Neomycin | F Mupirocin + HT61 | G Neomycin + HT61 |
| Cetyl alcohol | 7 | 7 | 7 | 7 | 7 | 7 | 7 | 7 |
| Stearyl alcohol | 7 | 7 | 7 | 7 | 7 | 7 | 7 | 7 |
| Cetomacrogol 1000 | 4 | 4 | 4 | 4 | 4 | 4 | 4 | 4 |
| Liquid paraffin | 16 | 16 | 16 | 16 | 16 | 16 | 16 | 16 |
| Water | 60 | 60 | 60 | 60 | 60 | 60 | 60 | 60 |
| Mupirocin calcium | 2 | 0 | 2 | 0 | 0 | 2 | 2 | 0 |
| Neomycin Sulfate | 0.5 | 0 | 0 | 0 | 0.5 | 0.5 | 0 | 0.5 |
| Xanthan gum | 0.5 | 0.5 | 0.5 | 0.5 | 0.5 | 0.5 | 0.5 | 0.5 |
| Benzyl alcohol | 2 | 2 | 2 | 2 | 2 | 2 | 2 | 2 |
| HT61 HCl | 1 | 0 | 0 | 1 | 0 | 0 | 1 | 1 |

The efficacy of each of the above formulations F017A, F022A, F022B, F022C, F022D, F022E, F022F, and F022G was assessed against S. aureus on pig skin. The S. aureus culture was grown overnight according to methods known in the art. The overnight culture was then spread on pig skin: 40 μl of culture was used for 2 cm3 of pig skin. Each of the formulations was then applied to the pig skin.

Figure 3:
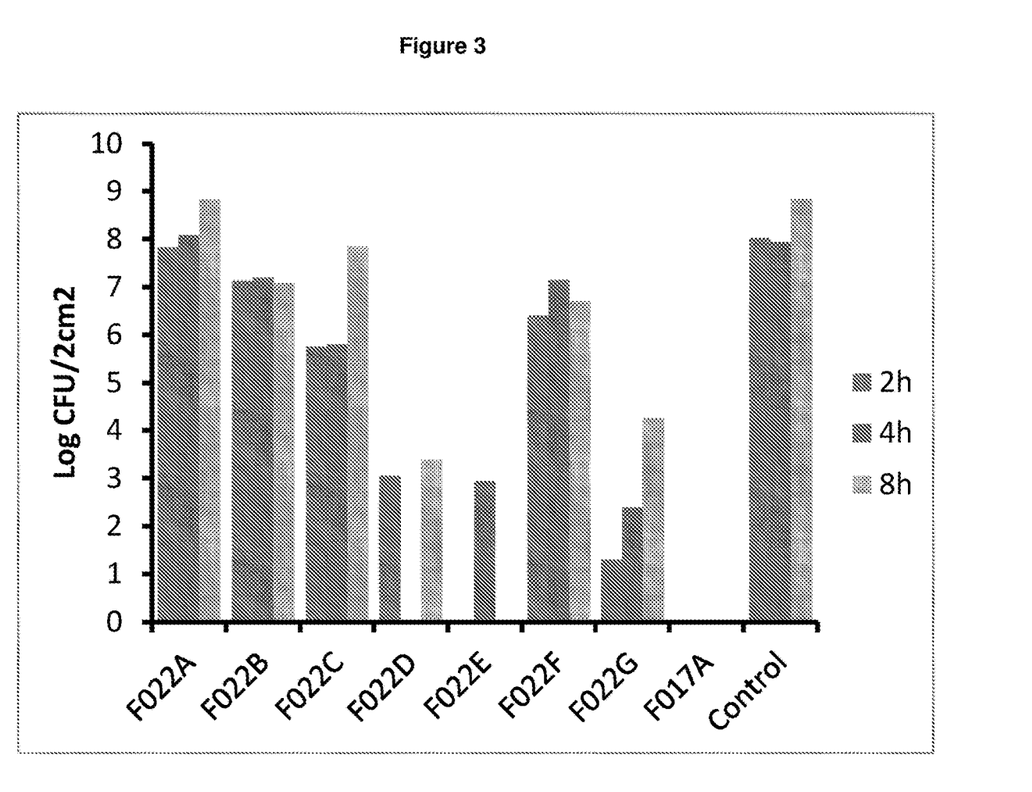

After 2 hours, 4 hours and 8 hours from application of each formulation, the pig skin was swabbed and bacteria on the swab were processed for CFU counting. The results for each of the above formulations as well as a control (where no triple combination was applied to the pig skin) are shown in FIG. 3.

The log kill values are shown in Table 6 below. The log kill of the inoculum was 7.6.

TABLE 6

| Formulation | Log Kill | | |
|---|---|---|---|
| | 2 h | 4 h | 8 h |
| F022A | −0.21 | −0.47 | −1.21 |
| F022B | 0.49 | 0.42 | 0.54 |
| F022C | 1.87 | 1.81 | −0.23 |
| F022D | 4.56 | 7.62 | 4.24 |
| F022E | 7.62 | 4.68 | 7.62 |
| F022F | 1.22 | 0.47 | 0.91 |
| F022G | 6.32 | 5.23 | 3.37 |
| F017A | 7.62 | 7.62 | 7.62 |
| Control | −0.41 | −0.33 | −1.21 |

Several comparisons can be made from the results of FIG. 3 and Table 6.

Firstly it can be seen that the triple combination formulation of the present invention (F017A) has a significantly and synergistically improved antimicrobial activity compared to each of the individual agents (F022B, F022C and F022D).

F017A resulted in complete kill (log kill of 7.62) of the bacteria on the pigs skin after 2 hours, whereas mupirocin had a log kill of 0.49, HT61 had a log kill of 1.87 and neomycin had a log kill of 4.56. The antimicrobial activity of the triple combination is also greater than the additive effect of the individual agents. As explained above, this means that the triple combination of the invention has synergistic antimicrobial activity.

The triple combination of the present invention (F017A) also has significantly improved antimicrobial activity compared to the double combinations: F022E, F022F and F022G. F022E is a formulation including mupirocin and neomycin. This double combination had a log kill of 7.62 (i.e. complete kill) after 2 hours, 4.68 after 4 hours and 7.62 after 8 hours. Unlike the triple combination (F017A), this formulation was therefore unable to maintain a complete kill of bacteria on the pig skin over a period of time.

F022F is a formulation including mupirocin and HT61, which had a log kill of only 0.91 after 9 hours, and F022G is a formulation including neomycin and HT61 which had a log kill of 6.32 after 2 hours but this decreased to 3.37 after 8 hours. F022G therefore failed to maintain an antimicrobial effect over the 8 hours.

The triple combination of the present invention not only provides a synergistic antimicrobial effect compared to the individual agents, but a sustained antimicrobial effect. It is therefore clearly advantageous for the treatment and/or prevention of microbial infections.

Of particular note is the low concentration of actives in the triple combination. HT61 for example is only included at a concentration of 0.5% w/w and yet the synergistic effect between the three actives results in a complete and sustained kill of bacteria.

The invention claimed is:

1. A combination comprising 4-methyl-8-phenoxy-1-(2-phenylethyl)-2,3-dihydro-1H-pyrrolo[3,2-c]quinoline or a pharmaceutically acceptable salt and/or solvate thereof, mupirocin or a pharmaceutically acceptable salt and/or solvate thereof and neomycin or a pharmaceutically acceptable salt and/or solvate thereof.

2. The combination according to claim 1, wherein the concentration of 4-methyl-8-phenoxy-1-(2-phenylethyl)-2,3-dihydro-1H-pyrrolo[3,2-c]quinoline or a pharmaceutically acceptable salt and/or solvate thereof is from about 0.01 to 2% by weight of the total combination.

3. The combination according to claim 1, wherein the concentration of mupirocin or a pharmaceutically acceptable salt and/or solvate thereof is from 0.2 to 2% by weight of the total combination.

4. The combination according to claim 1, wherein the concentration of neomycin or a pharmaceutically acceptable salt and/or solvate thereof is from 0.05 to 1% by weight of the total combination.

5. A method of treating a microbial infection in a mammal, wherein the method comprises administering a combination comprising 4-methyl-8-phenoxy-1-(2-phenylethyl)-2,3-dihydro-1H-pyrrolo[3,2-c]quinoline or a pharmaceutically acceptable salt and/or solvate thereof, mupirocin or a pharmaceutically acceptable salt and/or solvate thereof and neomycin or a pharmaceutically acceptable salt and/or solvate thereof.

6. The method according to claim 5 wherein the administering step includes killing multiplying, non-multiplying or clinically latent microorganisms associated with the microbial infection.

7. The method according to claim 5, wherein the concentration of 4-methyl-8-phenoxy-1-(2-phenylethyl)-2,3-dihydro-1H-pyrrolo[3,2-c]quinoline or a pharmaceutically acceptable salt and/or solvate thereof is from about 0.01 to 2% by weight of the total combination.

8. The method according to claim 5, wherein the concentration of mupirocin or a pharmaceutically acceptable salt and/or solvate thereof is from 0.2 to 2% by weight of the total combination.

9. The method according to claim 5, wherein the concentration of neomycin or a pharmaceutically acceptable salt and/or solvate thereof is from 0.05 to 1% by weight of the total combination.

10. The method according to claim 5, wherein the microbial infection is a bacterial infection.

11. The method according to claim 10, wherein the microbial infection is caused by Staphylococci, Streptococci, Bacillaceae, Enterobacteriaceae, *Haemophilis influenzae*, Enterococci, Mycobacteria.

12. The method according to claim 11, wherein the microbial infection is caused by *Staphylococcus aureus*.

13. The method according to claim 5, wherein the microbial infection is a fungal infection.

14. The method according to claim 13, wherein the microbial infection is caused by *Aspergillus fumigatus, Candida albicans, Cryptococcus neoformans, Histoplasma capsulatum* and *Pneumocystis jiroveci*.

15. A pharmaceutical composition comprising 4-methyl-8-phenoxy-1-(2-phenylethyl)-2,3-dihydro-1H-pyrrolo[3,2-c]quinoline or a pharmaceutically acceptable salt and/or solvate thereof, mupirocin or a pharmaceutically acceptable salt and/or solvate thereof and neomycin or a pharmaceutically acceptable salt and/or solvate thereof, and a pharmaceutically acceptable adjuvant, diluent or carrier.

16. The pharmaceutical composition according to claim 15, wherein the composition is formulated for oral, inhaled or topical administration.

* * * * *